(12) United States Patent
Tran et al.

(10) Patent No.: US 6,458,802 B1
(45) Date of Patent: Oct. 1, 2002

(54) ANTIDEPRESSANT AZAHETEROCYCLYMETHYL DERIVATIVES OF 2,3-DIHYDRO-1,4-DIOXINO [2,3-F] QUINOLINE

(75) Inventors: Megan Tran, Hoboken, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/095,505

(22) Filed: Mar. 12, 2002

Related U.S. Application Data
(60) Provisional application No. 60/275,564, filed on Mar. 14, 2001.

(51) Int. Cl.[7] .................. A61K 3/4741; C07D 491/02
(52) U.S. Cl. .................. 514/291; 546/90; 544/234; 514/248
(58) Field of Search .................. 514/291, 248; 546/90; 544/234

(56) References Cited

U.S. PATENT DOCUMENTS

| | | |
|---|---|---|
| 5,318,988 A | 6/1994 | Schohe-Loop et al. |
| 5,371,094 A | 12/1994 | Heine et al. |
| 5,741,789 A | 4/1998 | Hibschman et al. |
| 5,756,532 A | 5/1998 | Stack et al. |
| 5,869,490 A | 2/1999 | Stack |

OTHER PUBLICATIONS

Perez, V., et al., The Lancet, 349:1594–1597 (1997).

*Primary Examiner*—Charanjit S. Aulakh
(74) *Attorney, Agent, or Firm*—Rebecca R. Barrett

(57) ABSTRACT

Compounds of the formula:

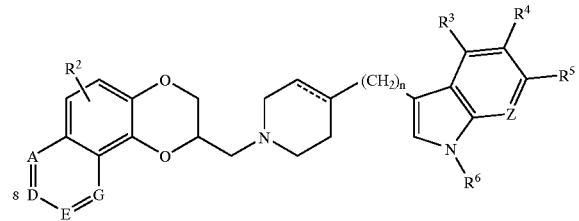

I are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder, social anxiety disorder, generalized anxiety disorder, obesity, eating disorders such as anorexia nervosa, bulimia nervosa, vasomotor flushing, cocaine and alcohol addiction, sexual dysfunction and related illnesses.

42 Claims, No Drawings

ANTIDEPRESSANT AZAHETEROCYCLYMETHYL DERIVATIVES OF 2,3-DIHYDRO-1,4-DIOXINO [2,3-F] QUINOLINE

This application claims priority from provisional application serial No. 60/275,564, filed on Mar. 14, 2001, now abandoned the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the formula:

I wherein
$R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms $R^6$ is hydrogen or alkyl of 1 to 6 carbon atoms;

A dotted line represents an optional double bond;

A and D are selected from carbon substituted by $R^1$ and nitrogen, provided that at least one of A and D is nitrogen;

E and G are carbon, substituted by $R^1$;

Z is N or $CR^7$; and n is an integer 0, 1 or 2; or pharmaceutically acceptable salts thereof.

A is preferably nitrogen.

$R^1$ is preferably hydrogen, hydroxy, halo, alkyl of 1 to 6 carbon atoms, amino, mono- or di-alkylamino in which each alkyl group has 1 to 6 carbon atoms. More preferably, $R^1$ is hydrogen, alkyl of 1 to 3 carbon atoms or amino. In still more preferred embodiments of the present invention $R^1$ is substituted at the 8-position of the 2,3-dihydro-1,4-dioxino [2,3-f]quinoline system.

$R^2$ is preferably hydrogen, hydroxy, halogen, cyano, trifluoromethyl, alkyl of 1 to 6 carbon atoms or alkoxy of one to six carbon atoms. In still more preferred embodiments of the present invention $R^2$ is hydrogen, halogen or alkoxy of 1 to 6 carbon atoms. In still more preferred embodiments of the present invention $R^2$ is hydrogen.

$R^3$, $R^4$, $R^5$ and $R^7$ are preferably independently selected from hydrogen, hydroxy, halo, cyano, carboxamido, alkyl of one to six carbon atoms, or alkoxy of one to six carbon atoms. In still more preferred embodiments of the present invention $R^3$, $R^4$, $R^5$ and $R^7$ are preferably independently selected from hydrogen, cyano or halogen.

$R^6$ is preferably hydrogen. Preferably n is 0 or 1. More preferably n is 0.

In still other preferred embodiments of the invention $R^2$ and $R^6$ are hydrogen, one of $R^3$, $R^4$, $R^5$ and $R^7$ is hydrogen, halogen or cyano, n is 0 and the dotted line represents a double bond.

In other preferred embodiments of the invention is provided compounds of Formula Ia.

Ia wherein $R^1$, $R^2$, $R^3$, $R^4$, n, Z and the dotted line are as described above.

This invention relates to both the R and S stereoisomers of the aminomethyl-2,3-dihydro-1,4-dioxino[2,3-f]

quinolines, as well as to mixtures of the R and S stereoisomers. Throughout this application, the name of the product of this invention, where the absolute configuration of the aminomethyl-2,3-dihydro-1,4-dioxino[2,3-f]quinolines is not indicated, is intended to embrace the individual R and S enantiomers as well as mixtures of the two. In some embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free", as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It is further recognized that tautomers of the claimed compounds may exist; for instance, when $R^1$ is hydroxy, a tautomeric form may exist. The present invention thus encompasses tautomeric forms of compounds of the present invention.

Alkyl, as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido, as used herein, refers to the group R—C(=O)—NH— where R is an alkyl group of 1 to 5 carbon atoms.

Alkanoyloxy, as used herein, refers to the group R—C(=O)—O— where R is an alkyl group of 1 to 5 carbon atoms.

Alkanesulfonamido, as used herein, refers to the group R—S(O)$_2$—NH— where R is an alkyl group of 1 to 6 carbon atoms.

Alkoxy, as used herein, refers to the group R—O— where R is an alkyl group of 1 to 6 carbon atoms.

Carboxamido, as used herein, refers to the group NH$_2$—C(=O)—. Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

2-[4-(5-Methoxy-1H-indol-3-yl)-3,6-dihydro-2H-pyridin-1-ylmethyl]-2,3-dihydro[1,4]dioxino[2,3-f]quinoline;

2-[4-(5-Fluoro-1H-indol-3-yl)-3,6-dihydro-2H-pyridin-1-ylmethyl]-2,3-dihydro[1,4]dioxino[2,3-f]quinoline;

[4-(5-Fluoro-1H-indol-3-ylmethyl)-piperidin-1-ylmethyl]-2,3-dihydro[1,4]-dioxino[2,3-f]quinoline;

2-[4-(1H-indol-3-yl)-3,6-dihydro-2H-pyridin-1-ylmethyl]-2,3-dihydro[1,4]dioxino[2,3-f]quinoline;

3-[1-(2,3-Dihydro[1,4]dioxino[2,3-f]quinolin-2-ylmethyl)-1,2,3,6-tetra-hydropyridin-4-yl]-1H-indole-5-carbonitrile;

3-[1-(2,3-Dihydro[1,4]dioxino[2,3-f]quinolin-2-ylmethyl)-1,2,3,6-tetra-hydropyridin-4-yl]-1H-indole-5-carboxylic acid amide;

2-[4-(5-Fluoro-1-methyl-1H-indol-3-yl)-3,6-dihydro-2H-pyridin-1-yl-methyl]-2,3-dihydro[1,4]dioxino[2,3-f]quinoline;

2-({4-[(5-Fluoro-1H-indol-3-yl)methyl]piperidin-1-yl}methyl)-8-methyl-2,3-dihydro[1,4]dioxino[2,3-f]quinoline;

2-[4-(1H-Indol-3-yl)-3,6-dihydro-2H-pyridin-1-ylmethyl]-8-methyl-2,3-dihydro[1,4]dioxino[2,3-f]quinoline;

2-[4-(6-Fluoro-1H-indol-3-yl)-3,6-dihydro-2H-pyridin-1-ylmethyl]-8-methyl-2,3-dihydro[1,4]dioxino[2,3-f]quinoline;

2-[4-(5-Fluoro-1H-indol-3-yl)-3,6-dihydro-2H-pyridin-1-ylmethyl]-8-methyl-2,3-dihydro[1,4]dioxino[2,3-f]quinoline;

2-[4-(1H-indol-3-yl)piperidin-1-ylmethyl]-8-methyl-2,3-dihydro[1,4]-dioxino[2,3-f]quinoline;

8-Ethyl-2-[(4-(1H-indol-3-yl)-3,6-dihydropyridin-1(2H)-yl)methyl]-2,3-dihydro[1,4]dioxino[2,3-f]quinoline;

8-Ethyl-2-[(4-(5-fluoro-1H-indol-3-yl)-3,6-dihydropyridin-1(2H)-yl)methyl]-2,3-dihydro[1,4]dioxino[2,3-f]quinoline;

6-Fluoro-2-[(4-(5-fluoro-1H-indol-3-yl)-3,6-dihydropyridin-1(2H)-yl)methyl]-2,3-dihydro[1,4]dioxino[2,3-f]quinoline;

6-Fluoro-2-[4-(1H-indol-3-yl)-3,6-dihydro-2H-pyridin-1-ylmethyl]-2,3-dihydro[1,4]dioxino[2,3-f]quinoline;

2-[4-(5-Fluoro-1H-indol-3-yl)-3,6-dihydro-2H-pyridin-1-ylmethyl]-6-methoxy-2,3-dihydro[1,4]dioxino[2,3-f]quinoline;

2-[4-(5-Fluoro-1H-indol-3-yl)-3,6-dihydro-2H-pyridin-1-ylmethyl]-2,3-dihydro-[1,4]dioxino[2,3-f]quinolin-8-ylamine;

2-({4-[(7-Ethyl-1H-indol-3-yl)methyl]piperidin-1-yl}methyl)-8-methyl-2,3-dihydro[1,4]dioxino[2,3-f]quinoline 2-({4-[(6-Chloro-1H-indol-3-yl)methyl]piperidin-1-yl}methyl)-8-methyl-2,3-dihydro[1,4]dioxino[2,3-f]quinoline 2-[4-(7-Fluoro-1H-indol-3-yl)-3,6-dihydro-2H-pyridin-1-ylmethyl]-8-methyl-2,3-dihydro[1,4]dioxino[2,3-f]quinoline 2-[4-(5-Methyl-1H-indol-3-yl)-3,6-dihydro-2H-pyridin-1-ylmethyl]-8-methyl-2,3-dihydro[1,4]dioxino[2,3-f]quinoline;

2-[4-(1H-Indol-3-yl)-3,6-dihydro-2H-pyridin-1-ylmethyl]-9-methyl-2,3-dihydro[1,4]dioxino[2,3-f]quinoline, and 8-Ethyl-2-[4-(1H-indol-3-yl)-piperidin-1-ylmethyl]-2,3-dihydro-[1,4]dioxino[2,3-f]quinoline; and pharmaceutically acceptable salts thereof.

Further in accordance with the present invention are provided compounds of Formula II

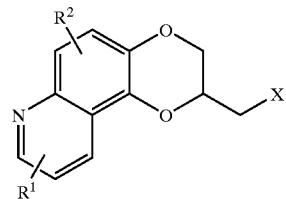

wherein
- $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- $R^2$ is hydrogen, hydroxy, halo, cyano, carboxamido, carboalkoxy of two to six carbon atoms, alkyl of 1 to 6 carbon atoms, trifluoromethyl, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- X is halogen, hydroxy, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms.

Specific examples of compounds of Formula II are
2,3-Dihydro[1,4]dioxino[2,3-f]quinolin-2-ylmethyl 4-methylbenzenesulfonate;
(8-Methyl-2,3-dihydro[1,4]dioxino[2,3-f]quinolin-2-yl)methyl 4-methylbenzenesulfonate;
(8-Ethyl-2,3-dihydro[1,4]dioxino[2,3-f]quinolin-2-yl)methyl 4-methylbenzenesulfonate;
6-Fluoro-2,3-dihydro[1,4]dioxino[2,3-f]quinolin-2-ylmethyl 4-methylbenzenesulfonate;
6-Methoxy-2,3-dihydro[1,4]dioxino[2,3-f]quinolin-2-ylmethyl 4-methylbenzenesulfonate;
(8-Amino-2,3-dihydro[1,4]dioxino[2,3-f]quinolin-2-yl) methyl 4-methylbenzenesulfonate; and
9-Methyl-2,3-dihydro[1,4]dioxino[2,3-f]quinolin-2-yl) methyl 4-methylbenzenesulfonate.

Compounds of Formula II are particularly useful for the production of compounds of Formula Ia.

Compounds of the present invention are prepared in accordance with the following general description and specific examples. Variables used are as defined for Formula I, unless otherwise noted.

The 2-azaheterocyclylmethyl-2,3-dihydro-1,4-dioxino[2,3-f]quinolines in which $R^1$ is H are prepared as illustrated in Scheme I. Specifically, the appropriately substituted nitroguaiacol (1) is alkylated with allyl bromide in the presence of a suitable base such as sodium hydride to produce (2) and then demethylated by a reagent such as sodium hydroxide. The resulting 4-nitro-2-allyloxyphenol (3) is then alkylated with glycidyl

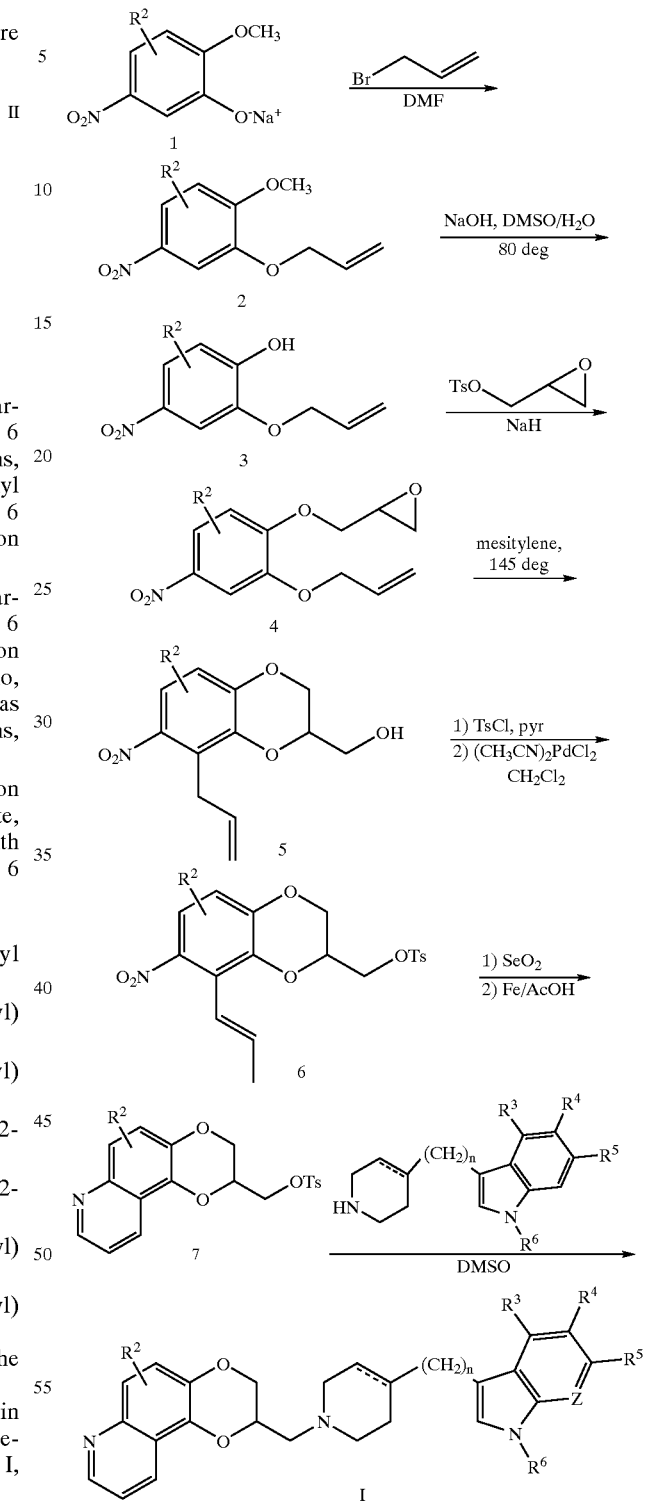

tosylate or an epihalohydrin in the presence of a base such as sodium hydride to produce (4) and heated in a high boiling solvent such as mesitylene or xylene to effect both rearrangement of the allyl group and cyclization to the dioxan ring. The resulting primary alcohol (5) is converted to the tosylate by reaction with p-toluenesulfonyl chloride in the presence of a tertiary amine or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene to produce (6). Allylic oxidation with selenium dioxide in refluxing dioxane/water gives the o-nitrocinnamaldehyde, which upon reduction with iron in acetic acid cyclizes to the 2,3-dihydro-1,4-dioxino[2,3-f] quinoline-2-methyl-tosylate or halide (7). Replacement of the tosylate or halide with the appropriately substituted azaheterocycle in some high boiling solvent such as dimethyl sulfoxide gives the title compounds of Formula Ia.

Compounds of the invention in which $R^1$ is alkyl may be prepared from the nitro olefin described in Scheme I in the manner described in Scheme II. The rearranged olefin (6) is treated sequentially with ozone and a tertiary amine or with osmium tetroxide and sodium periodate to give the o-nitrobenzaldehyde (8).

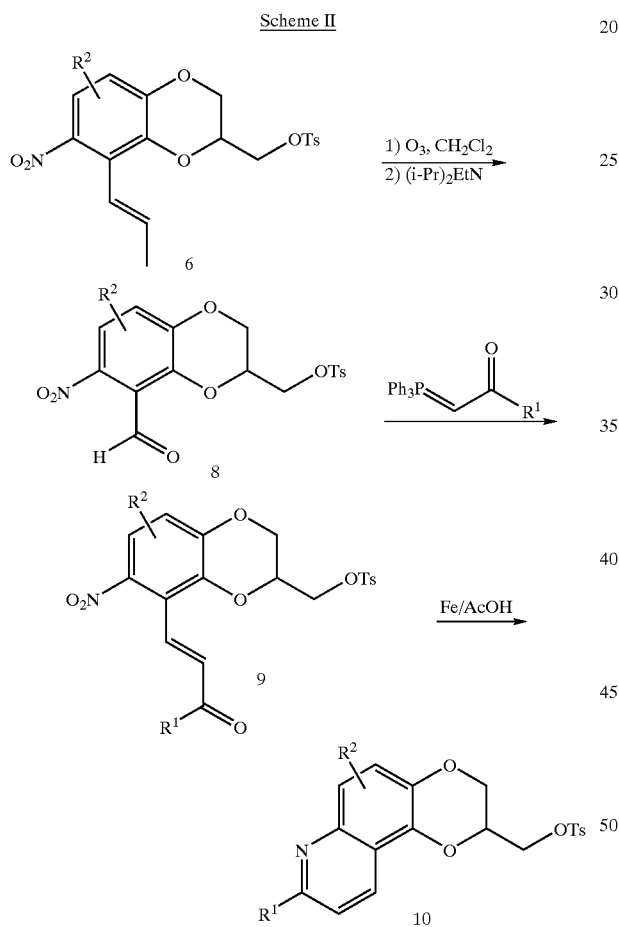

Scheme II

Condensation with the appropriate triphenylphosphoranylidene ketone under Wittig conditions gives the o-nitrostyryl ketone (9), which upon reduction by iron in acetic acid, cyclizes to the corresponding 2,3-dihydro-1,4-dioxino[2,3-f]quinoline-2-methyltosylate (10). Replacement of the tosylate with the appropriately substituted azaheterocycle as above gives the title compounds of the invention.

Substitution of trimethyl phosphonoacetate for the triphenylphosphoranylidene ketone in the Wittig procedure above, followed by reduction of the nitro group with tin (II) chloride and cyclization in acid gives the compounds of the invention in which $R^1$ is hydroxy. Alkylation of this hydroxy derivative by a suitable alkyl halide or tosylate in the presence of base gives the compounds of the invention in which $R^1$ is alkoxy. Treatment of the hydroxy derivative with an inorganic acid chloride such as phosphoryl chloride or bromide gives the compounds of the invention in which $R^1$ is halo. Substitution of diethyl cyanomethylphosphonate for the triphenyl-phosphoranylidene ketone in the Wittig procedure above, followed by reduction of the nitro group with tin (II) chloride and cyclization in acid gives the compounds of the invention in which $R^1$ is amino.

The o-nitrobenzaldehyde (8) used in the Wittig chemistry described in Scheme II may be alternatively prepared as shown in Scheme III. The appropriate mono-allylated catechol (11) is elaborated with glycidyl tosylate as described above to produce (12) and rearranged in refluxing mesitylene. Cyclization to the benzodioxan methanol is Scheme III

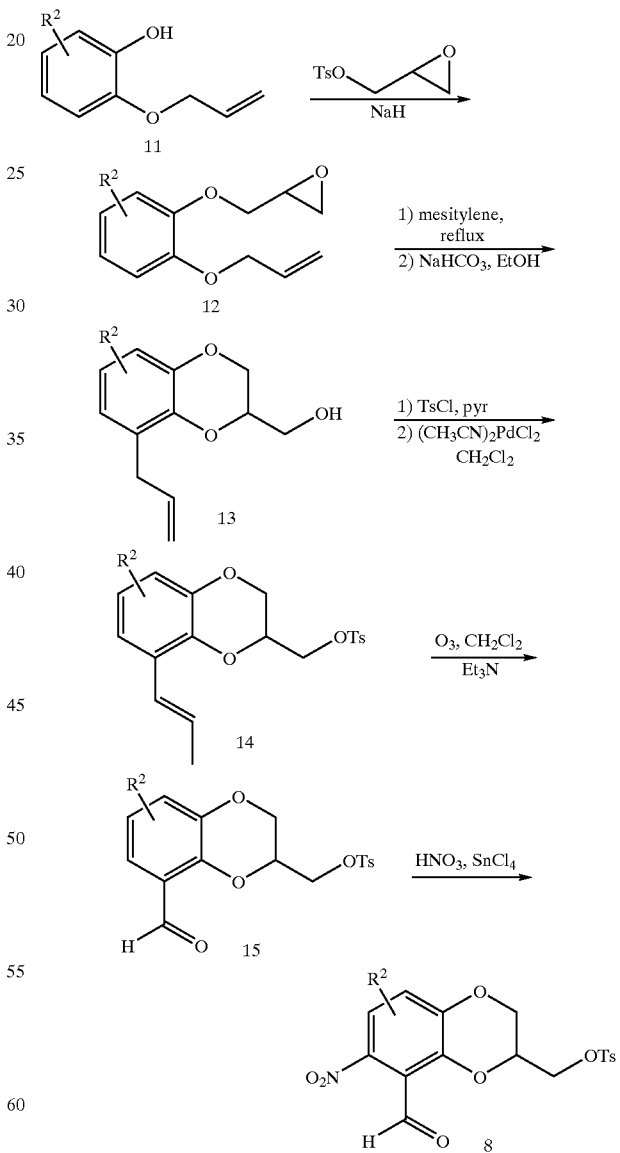

effected by treatment with sodium bicarbonate in ethanol and the alcohol (13) is converted to the tosylate or halide (14) as described in Scheme (I). After rearrangement of the double bond by treatment with catalytic bis-acetonitrile palladium chloride in refluxing methylene chloride to produce and cleavage with ozone or osmium tetroxide/sodium periodate as described above, the resulting aldehyde (15) is regioselectively nitrated with a combination of nitric acid and tin (IV) chloride to produce (8).

Compounds of the invention in which $R^2$ is attached to position 6 of the 2,3-dihydro-1,4-dioxino[2,3-f]quinoline may be alternatively prepared by a variation of the Skraup quinoline synthesis according to Scheme IV. The appropriately substituted benzodioxan methyltosylate (16) is nitrated under standard conditions with nitric acid in a solvent such as dichloroethane and the resulting nitro compound (17)

Scheme IV

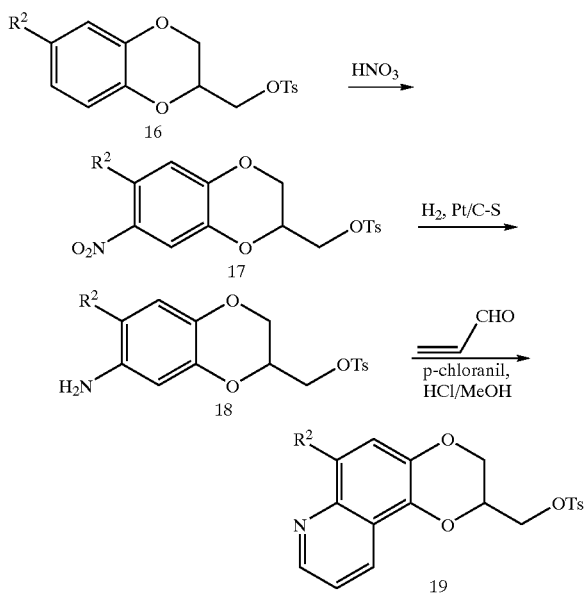

reduced by treatment with hydrogen in the presence of a catalyst such as platinum on sulfide carbon. Treatment of the resulting aniline (18) with acrolein in the presence of hydrogen chloride and an oxidant such as p-chloranil or naphthoquinone gives the corresponding 2,3-dihydro-1,4-dioxino[2,3-f]quinoline (19). Replacement of the tosylate with the appropriately substituted azaheterocycle as above gives the title compounds of the invention.

The guaiacols, catechols, benzodioxan methyltosylates and azaheterocycles appropriate to the above chemistry are known compounds or can be prepared by one schooled in the art.

In yet another method, compounds of the present invention may be prepared in accordance with Scheme V.

V

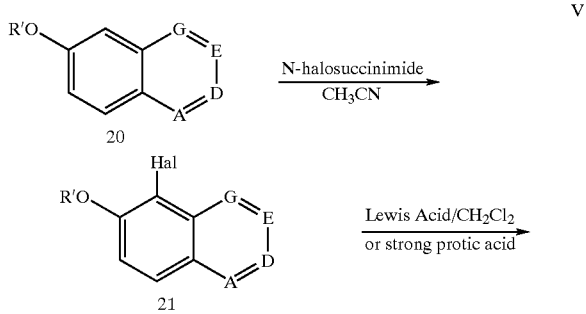

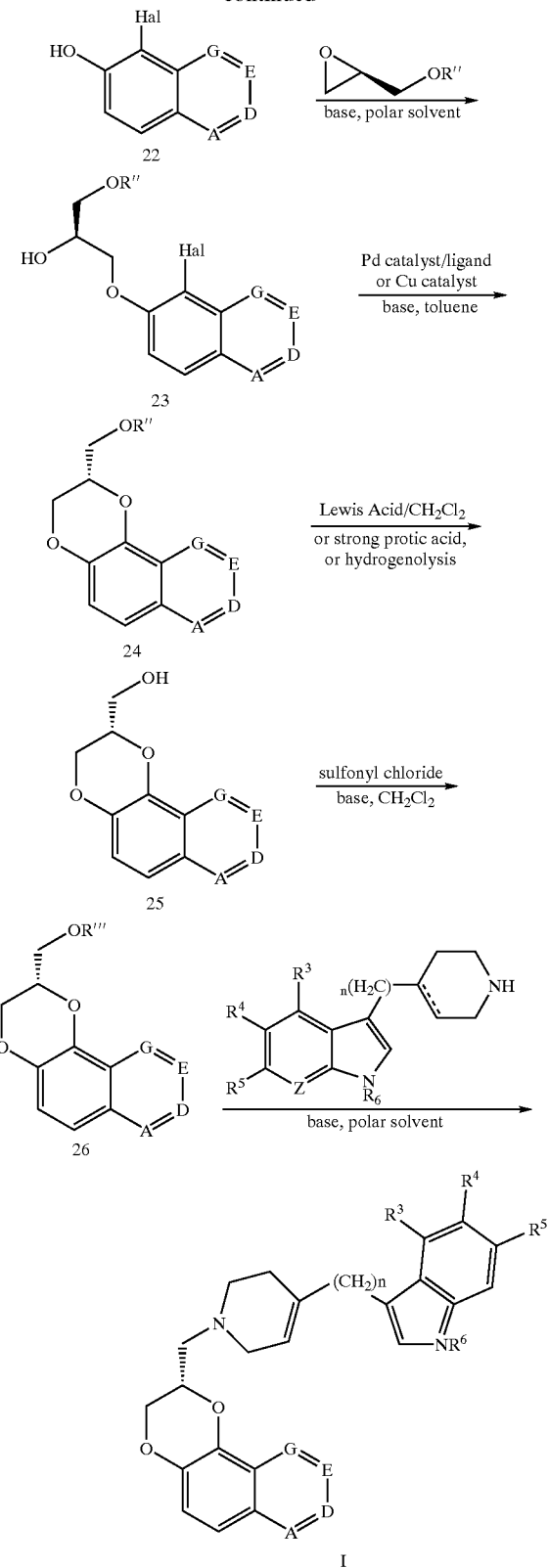

The synthesis of compound I is comprised of steps that begin with halogenation of 20 where R' is alkyl of 1–6 carbon atoms, with reagents such as N-halosuccinimide in acetonitrile to give 21 (where Hal is halogen such as Br, Cl or I). Deprotecting 21 with Lewis acids such as boron tribromide, boron trichloride, aluminum trichloride, ferric chloride, or trimethylsilyl iodide in a suitable solvent such as methylene chloride, or with strong protic acids such as HBr and HCl gives the salt 22. Free base 22 may be obtained by neutralization with an Amberlyst A-21 resin slurry in polar solvents such as ethanol or methanol.

Alkylation of 22, either as the free base or as the salt, with benzyl or substituted benzyl protected glycidyl ethers

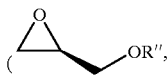

where R" is benzyl, substituted benzyl such as 4-bromobenzyl, 3,4-dimethoxybenzyl, 2- or 4-nitrobenzyl, or 4-methoxybenzyl) in suitable polar solvents such as DMSO, DMF, or DMA in the presence of bases such as sodium carbonate, potassium carbonate, or triethylamine gives 23. 23 was then cyclized using palladium catalysts such as tris(dibenzylideneacetone)dipalladium, tetrakis (triphenylphosphine)palladium, or palladium acetate with ligands from the group consisting of (±) BINAP and separate enantiomers thereof, (±) Tol-BINAP and separate enantiomers thereof; 1-1'-bis(diphenylphosphino) ferrocene, 1,3-bis(diphenylphosphino)propane, and 1,2 bis(diphenylphosphino)ethane in the presence of bases such as NaH, LiH, KH, potassium carbonate, sodium carbonate, titanium carbonate, cesium carbonate, potassium t-butoxide or potassium phosphate tribasic in suitable solvent such as toluene, or alternatively, with copper catalyst such as copper iodide in the presence of bases such NaH, LiH, KH in a suitable solvent such as toluene to afford 24.

Deprotection of quinoline 24 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents such as hydrogen, cyclohexene, methyl cyclohexene, or ammonium formate gives quinaldine 25. The hydroxyl moiety of 25 can be activated with sulfonyl chloride such as p-toluenesulfonyl chloride, methanesulfonyl chloride, 2-, 3- or 4-nitrobenzenesulfonyl chloride, or 2- or 4-bromobenzenesulfonyl chloride in the presence of bases such as triethylamine or pyridine in suitable solvents such as methylene chloride, THF, or toluene to afford 26 where R'" is sulfonate such as p-toluenesulfonate, methanesulfonate, 2-, 3-, or 4-nitrobenzenesulfonate, or 2- or 4-bromobenzenesulfonate. The final coupling of 26 with azaheterocycles appropriate to the invention, in the presence of bases such as Hünig's base (diisopropyl ethylamine), potassium carbonate, or sodium carbonate in polar solvents such as THF, dioxane, DMSO, DMF, or DMA affords final compound 1.

The compounds of the invention may be resolved into their enantiomers by conventional methods or, preferably, the individual enantiomers may be prepared directly by substitution of (2R)-(−)-glycidyl 3-nitrobenzene-sulfonate or tosylate (for the S benzodioxan methanamine) or (2S)-(+)-glycidyl 3-nitrobenzene-sulfonate or tosylate (for the R enantiomer) in place of epihalohydrin or racemic glycidyl tosylate in the procedures above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_j$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin $5HT_{1A}$ receptor was established by testing the claimed compound's ability to displace [$^3$H] 8-OH-DPAT (dipropylamino-tetralin) from the $5HT_{1A}$ serotonin receptor following a modification of the procedure of Hall et al., J. Neurochem. 44, 1685 (1985) which utilizes CHO cells stably transfected with human $5HT_{1A}$ receptors. The $5HT_{1A}$ affinities for the compounds of the invention are reported below as $K_j$'s.

Antagonist activity at $5HT_{1A}$ receptors was established by using a $^{35}$S-GTPγS binding assay similar to that used by Lazareno and Birdsall (Br. J. Pharmacol. 109: 1120, 1993), in which the test compound's ability to affect the binding of 35S-GTPγS to membranes containing cloned human $5HT_{1A}$ receptors was determined. Agonists produce an increase in binding whereas antagonists produce no increase but rather reverse the effects of the standard agonist 8-OH-DPAT. The test compound's maximum inhibitory effect is represented as the $1_{max}$, while its potency is defined by the $IC_{50}$.

The results of the three standard experimental test procedures described in the preceding three paragraphs were as follows:

| Compound | 5-HT Transporter Affinity KI (nM) | $5HT_{1A}$ Receptor Affinity KI (nM) | $5HT_{1A}$ Function $IC_{50}$ (nM) ($I_{max}$) |
|---|---|---|---|
| Example 1 | 54.00 | 9.29 | 322.0 (100) |
| Example 2 | 2.82 | 9.88 | 242.7 (100) |
| Example 3 | 1.20 | 17.18 | 120.0 (90.0) |
| Example 4 | 3.38 | 4.84 | 226.0 (87.0) |
| Example 5 | 2.54 | 19.26 | |
| Example 6 | 3.54 | 9.44 | |
| Example 7 | 8.50 | 14.72 | 1076.0 (100) |
| Example 8 | 2.56 | 7.24 | |
| Example 9 | 2.34 | 3.02 | 56.7 (98.3) |
| Example 10 | 8.00 | 6.70 | 259.0 (100) |
| Example 11 | 5.51 | 13.25 | 120.5 (100) |
| Example 12 | 2.39 | 9.98 | 85.7 (100) |
| Example 13 | 4.90 | 6.82 | 162.0 (88.7) |
| Example 14 | 14.00 | 15.40 | 166.0 (100) |
| Example 15 | 1.50 | 36.44 | 1031.0 (100) |
| Example 16 | 21.00 | 55.94 | |
| Example 17 | 4.74 | 316.85 | 1414.0 (100) |
| Example 18 | 0.66 | 10.94 | 84.9 (100) |
| Example 19 | 11.00 | 7.38 | 169.0 (100) |
| Example 20 | 7.00 | 25.45 | 666.1 (100) |
| Example 21 | 2.94 | 7.75 | 51.7 (100) |
| Example 22 | 59.00 | 34.67 | 503.4 (100) |
| Example 23 | 28.00 | 7.76 | |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses. Moreover, the compounds of this invention have potent affinity for and antagonist activity at brain $5HT_{1A}$ serotonin receptors. Recent clinical trials employing drug mixtures (eg, fluoxetine and pindolol) have demonstrated a more rapid onset of antidepressant efficacy for a treatment combining SSRI activity and $5HT_{1A}$ antagonism (Blier and Bergeron, 1995; F. Artigas et. al., 1996; M. B. Tome et. al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes of sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the pat ient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I and la. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-methoxynitrobenzene 97.5 g (0.51 mole) of the sodium salt of 5-nitroguaiacol was dissolved in one Vliter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tic with 1:1 hexane/methylene chloride) (R)-2-(2-allyloxy-4-nitrophenoxymethyl)-oxirane (m.p. 64° C.).

Elemental Analysis for: $C_{12}H_{13}NO_5$; Calc'd: C, 57.37; H, 5.21; N, 5.58; Found: C, 57.50; H, 5.21; N, 5.43.

INTERMEDIATE 4

(8-Allyl-7-nitro-2,3-dihydro-benzo(1.4)dioxin-2-yl)-methanol (R)-2-(2-Allyloxy-4-nitrophenoxymethyl)-oxirane (20 g, 80 mmoles) pre-pared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$; Calc'd: C, 57.37; H, 5.21; N, 5.58; Found: C, 57.26; H, 5.20; N, 5.35.

INTERMEDIATE 5

Toluene-4-sulfonic Acid 8-allyl-7-nitro-2,3-dihydro-benzo(1,4)dioxin-2-ylmethyl Ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$; Calc'd: C, 56.29; H, 4.72; N, 3.45; Found: C, 56.13; H, 4.58; N, 3.44.

INTERMEDIATE 6

{7-Nitro-8-[1-propenyl]-2,3-dihydro-1,4-benzodioxin-2-yl}methyl 4-Methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1, 4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$; Calc'd: C, 56.29; H, 4.72; N, 3.45; Found: C, 56.12; H, 4.64; N, 3.39.

INTERMEDIATE 7

{7-Nitro-8-[3-oxo-1-propenyl[-2,3-dihydro-1,4-benzodioxin-2-yl}methyl 4-Methylbenzenesulfonate {(2R)-7-nitro-8-[1-propenyl]-2,3-dihydro-1,4-benzodioxin-2-yl}methyl 4-methylbenzenesulfonate (6.15 g, 15.2 mmole) was dissolved in 180 mL of dioxane. Selenium dioxide (4.20 g, 37.9 mmole) was then added, followed by 0.70 mL of water. The heterogeneous mixture was heated at reflux under nitrogen for 5 hours. Upon cooling, the reaction was filtered and concentrated in vacuum to yield a dark yellow solid. This was dissolved in minimal ethyl acetate and column chromatographed on silica gel using 30% ethyl acetate in hexane as eluant to give 5.75 g of the (R)-enantiomer of the title compound as a light yellow solid (m.p. 138–140° C.).

Elemental Analysis for: $C_{19}H_{17}NO_8S$; Calc'd: C, 54.41; H, 4.09; N, 3.34; Found: C, 54.10; H, 3.85; N, 3.31.

INTERMEDIATE 8

2,3-Dihydro[1,4]dioxino[2,3-f]giuinolin-2-ylmethyl 4-Methylbenzenesulfonate

To a solution of {(2R)-7-nitro-8-[3-oxo-1-propenyl]-2,3-dihydro-1,4-benzo-dioxin-2-yl}methyl 4-methylbenzenesulfonate (3.50 g, 8.35 mmole) in 200 mL of acetic acid/ethanol (1:1) was added 2.35 g (42.1 mmole) of iron powder and the mixture was heated at reflux under nitrogen for 8 hours. After the reaction was complete, 150 mL of water was added and the mixture filtered through a pad of celite. The filtrate was neutralized with saturated sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 1.85 g of the (R)-enantiomer of the title compound as a yellow oil. $^1$H-NMR (CDCl$_3$): doublet 8.8 δ (1 H); doublet 8.2 δ (1 H); doublet 7.8 δ (2 H); doublet 7.6 δ (1 H); multiplet 7.35 δ (1 H); multiplet 7.25 δ (3 H); multiplet 4.6 δ (1 H); multiplet 4.3–4.4 δ (3 H); multiplet 4.2 δ (1 H); singlet 2.4 δ (3 H).

EXAMPLE 1

2-[4-(5-Methoxy-1H-indol-3-yl)-3,6-dihydro-2H-pyridin-1-ylmethyl]-2,3-dihydro[1,4]dioxinor2,3-f]guinoline (2R)-2,3-Dihydro[1,4]dioxino[2,3-f]quinolin-2-ylmethyl 4-methylbenzenesulfonate (0.62 g, 1.67 mmole) and 5-methoxy-3-(1,2,3,6-tetrahydro-4-pyridinyl)-1H-indole (1.33 g, 5.83 mmole) were combined in 40 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first methylene chloride to elute impurities and then 5% methanol in methylene chloride to elute the product, 0.31 g of a yellow oil. The oil was recrystallized from ethanol with the addition of 0.10 g of fumaric acid to give 0.155 g of the (S)-enantiomer of the title compound as a yellow monofumarate salt (m.p. 170° C.).

Elemental Analysis for: $C_{26}H_{25}N_3O_3 \cdot C_4H_4O_4$; Calc'd: C, 66.29; H, 5.38; N, 7.73; Found: C, 66.56; H, 5.82; N, 7.77.

EXAMPLE 2

2-[4-(5-Fluoro-1H-indol-3-yl)-3,6-dihydro-2H-pyridin-1-ylmethyl]-2,3-dihydro]1,4dioxino[2,3-f]quinoline (2R)-2,3-Dihydro[1,4]dioxino[2,3-f]quinolin-2-ylmethyl 4-methylbenzenesulfonate (0.45 g, 1.21 mmole) and 5-fluoro-3-(1,2,3,6-tetrahydro-4-pyridinyl)-1H-indole (0.79 g, 3.63 mmole) were combined in 50 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first methylene chloride to elute impurities and then 3% methanol in methylene chloride to elute 0.13 g of the (S)-enantiomer of the title compound as a light yellow hemihydrate (m.p. 184° C.).

Elemental Analysis for: $C_{25}H_{22}FN_3O_2 \cdot 0.5$ HO; Calc'd: C, 70.74; H, 5.46; N, 9.90; Found: C, 70.92; H, 5.41; N, 9.75.

EXAMPLE 3

[4-(5-Fluoro-1H-indol-3-ylmethyl)-piperidin-1-ylmethyl]-2,3-dihydro[1,4dioxino[2,3-f]quinoline (2R)-2,3-Dihydro[1,4]dioxino[2,3-f]quinolin-2-ylmethyl 4-methylbenzenesulfonate (0.46 g, 1.24 mmole) and 5-fluoro-3-(4-piperidinylmethyl)-1H-indole (1.00 g, 4.32 mmole) were combined in 40 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first methylene chloride to elute impurities and then 3% methanol in methylene chloride to elute 0.200 g of the product as a yellow oil. The oil was crystallized from isopropanol with the addition of 0.040 g of oxalic acid to give 0.107 g of the (S)-enantiomer of the title compound as a light red solid (m.p. 184° C.), which contained both water and isopropanol.

Elemental Analysis for: $C_{26}H_{26}FN_3O_2 \cdot 1.5$ $C_2H_2O_4 \cdot 0.8$ $H_2O \cdot 0.55$ $C_3HO$; Calc'd: C, 59.95; H, 5.75; N, 6.84; Found: C, 59.65; H, 5.59; N, 6.70.

EXAMPLE 4

2-[1,4-(1H-indol-3-yl)-3,6-dihydro-2H-pyridin-1-ylmethyl]-2,3-dihydro[1,4]dioxino[2,3-f]quinoline (2R)-2,3-Dihydro[1,4]dioxino[2,3-f]quinolin-2-ylmethyl 4-methylbenzenesulfonate (0.50 g, 1.34 mmole) and 3-(1,2,3,6-tetrahydro-4-pyridinyl)-1H-indole (0.72 g, 3.65 mmole) were combined in 60 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first ethyl acetate to elute impurities and then 3% methanol in ethyl acetate to elute 0.110 g of the product as a light yellow solid. This was recrystallized from ethanol to give 0.050 g of the (S)-enantiomer of the title compound as a light yellow solid hemihydrate (m.p. 217° C.).

Elemental Analysis for: $C_{25}H_{23}N_3O_2 \cdot 0.5$ $H_2O$; Calc'd: C, 73.87; H, 5.95; N, 9.84; Found: C, 74.14; H, 5.90; N, 10.10.

EXAMPLE 5

3-[1-(2,3-Dihydro[1,4]dioxino[2,3-f]quinolin-2-ylmethyl)-1,2,3,6-tetrahydropyridin-4-yl]-1H-indole-5-carbonitrile (2R)-2,3-dihydro[1,4]dioxino[2,3-f]quinolin-2-ylmethyl 4-methylbenzenesulfonate (0.51 g, 1.37 mmole) and 3-(1,2, 3,6-tetrahydro-4-pyridinyl)-1H-indole-5-carbonitrile (0.42 g, 1.88 mmole) were combined in 70 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first 90% hexane/ethyl acetate to elute impurities and then 1:1 hexane/ethyl acetate to elute 0.240 g of the product as a yellow oil. This was crystallized from ethanol with the addition of 0.050 g of fumaric acid to give 0.160 g of the (S)-enantiomer of the title compound as a yellow solid fumarate (m.p. 159–161° C.) containing 0.80 equivalents of water.

Elemental Analysis for: $C_{26}H_{22}N_4O_2 \cdot C_4H_4O_4 \cdot 0.8\ H_2O$; Calc'd: C, 65.16; H, 5.03; N, 10.13; Found: C, 64.81; H, 4.85; N, 9.88.

EXAMPLE 6

3-[1-(2,3-Dihydro[1,4]dioxino[2,3-f]qiuinolin-2-ylmethyl)-1,2,3,6-tetrahydropyridin-4-yl]-1H-indole-5-carboxylic Acid Amide (2R)-2,3-Dihydro[1,4]dioxino[2,3-f]quinolin-2-ylmethyl 4-methylbenzenesulfonate (0.50 g, 1.35 mmole) and 3-(1,2,3,6-tetrahydro-4-pyridinyl)-1H-indole-5-carboxamide (0.52 g, 2.16 mmole) were combined in 50 mL of DMSO and heated at 75–80° C. under nitrogen for 6 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first methylene chloride to elute impurities and then 6% methanol in methylene chloride to elute 0.340 g of the product as a yellow foam. This was crystallized from ethanol with the addition of 0.10 g of fumaric acid to give 0.188 g of the (S)-enantiomer of the title compound as a yellow solid fumarate monohydrate (m.p. 219° C.).

Elemental Analysis for: $C_{26}H_{24}N_4O_3 \cdot C_4H_4O_4 \cdot H_2O$; Calc'd: C, 62.71; H, 5.26; N, 9.75; Found: C, 62.86; H, 5.13; N, 9.61.

EXAMPLE 7

2-[4-(5-Fluoro-1-methyl-1H-indol-3-yl)-3,6-dihydro-2H-pyridin-1-ylmethyl]-2,3-dihydro[1,4]dioxino[2,3-f]qiuinoline (2S)-2-[4-(5-Fluoro-1H-indol-3-yl)-3,6-dihydro-(2H)-pyridin-1-yl]methyl]-2,3-dihydro[1,4]dioxino[2,3-f]quinoline (0.25 g, 0.60 mmole) was dissolved in 5.0 mL of dimethylformamide and 0.080 g (2.0 mmole) of 60% sodium hydride/mineral oil dispersion was added. The mixture was stirred at room temperature under nitrogen for 30 min, and then 0.112 g (0.60 mmole) of methyl tosylate added. The mixture was heated for 4 hours at 65° C. under nitrogen and then allowed to cool. The mixture was then concentrated in vacuum and the residue column chromatographed on silica gel with 1% methanol in methylene chloride as eluant to give 0.090 g of product as a yellow film. This was dissolved in hot methanol and treated with excess 4 N isopropanolic HCl to give 0.020 g of the (S)-enantiomer of the title compound as a yellow solid dihydrochloride, 2.5 hydrate.

Elemental Analysis for: $C_{26}H_{24}FN_3O_2 \cdot 2\ HCl\ 2.5\ H_2O$; Calc'd: C, 57.04; H, 5.71; N, 7.68; Found: C, 56.62; H, 5.59; N, 7.44.

INTERMEDIATE 9

(8-Formyl-7-nitro-2,3-dihydro-14-benzodioxin-2-yl)methyl 4-Methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 minutes and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4–4.6 δ (2 H); multiplet 4.2 δ (3 H); singlet 2.4 δ (3 H).

INTERMEDIATE 10

{7-Nitro-8-[(E)-3-oxo-1-butenyl]-2,3-dihydro-1,4-benzodioxin-2-yl}methyl 4-Methylbenzenesulfonate To a solution of 3.00 g (7.37 mmole) of [(2R)-8-formyl-7-nitro-2,3-dihydro-1,4-benzodioxin-2-yl]methyl 4-methylbenzenesulfonate in 250 mL of toluene was added 2.90 g (9.10 mmole) of 1-triphenylphosphoranylidene-2-propanone. The mixture was stirred at room temperature under nitrogen for 5 hours, during which time some product precipitated from solution. The solvent was removed in vacuum and the crude residue was column chromatographed on silica gel with methylene chloride as eluant to give 3.0 g of the (R)-enantiomer of the title compound as a yellow solid. $^1$H-NMR (CDCl$_3$): doublet 7.8 δ (2 H); doublet 7.6 δ (1 H); doublet 7.5 δ (2 H); doublet 7.4 δ (2 H); doublet 6.95 δ (1 H); doublet 6.6 δ (1 H); multiplet 4.5 δ (1 H); doublet of doublets 4.0 δ (1 H); multiplet 4.2 δ (3 H); singlet 2.45 δ (3 H); singlet 2.4 δ (3 H).

INTERMEDIATE 11

(8-Methyl-2,3-dihydro[1,4]dioxino[2,3-f]quinolin-2-yl)methyl 4-Methylbenzenesulfonate To a solution of {(2R)-7-nitro-8-[(E)-3-oxo-1-butenyl]-2,3-dihydro-1,4-benzo-dioxin-2-yl}methyl 4-methylbenzenesulfonate (3.40 g, 7.83 mmole) in 200 mL of acetic acid/ethanol (3:2) was added 2.25 g (40.2 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 2.5 g of the (R)-enantiomer of the title compound as a yellow oil. $^1$H-NMR (CDCl$_3$): doublet 8.1 δ (1 H); doublet 7.6 δ (2 H); doublet 7.45 δ (1 H); multiplet 7.2 δ (4 H); multiplet 4.6 δ (1 H); multiplet 4.3 δ (3 H); multiplet 4.1 δ (1 H); singlet 2.5 δ (3H); singlet 2.4 δ (3 H).

EXAMPLE 8

2-({4-[(5-Fluoro-1H-indol-3-yl)methyl]piperidin-1-yl}methyl)-8-methyl-2,3-dihydro[1,4]dioxino[2,3-f]quinoline To a solution of (2R)-8-methyl-2,3-dihydro[1,4]dioxino[2,3-f]quinolin-2-ylmethyl 4-methylbenzenesulfonate (0.61 g, 1.58 mmole) and potassium carbonate (0.60 g, 4.34 mmole) in 30 mL of 1:1 THF/DMF was added 1.00 g (4.32 mmole) of 5-fluoro-3-(4-piperidinylmethyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute 0.118 g of the (S)-enantiomer of the title compound as a white solid (m.p. 91–92° C.) containing 0.60 equivalents of water.

Elemental Analysis for: C$_{27}$H$_{28}$FN$_3$O$_2$.0.6 H$_2$O; Calc'd: C, 71.06; H, 6.45; N, 9.21; Found: C, 70.79; H, 6.19; N, 9.04.

EXAMPLE 9

2-[4-(1H-Indol-3-yl)-3,6-dihydro-2H-yridin-1-ylmethyl]-8-methyl-2,3-dihydro[1,4]dioxino[2,3-f]quinoline To a solution of (2R)-8-methyl-2,3-dihydro[1,4]dioxino[2,3-f]quinolin-2-ylmethyl 4-methylbenzenesulfonate (7.02 g, 18.1 mmole) and potassium carbonate (5.71 g, 41.3 mmole) in 250 mL of 1:1 THF/DMF was added 10.7 g (54.5 mmole) of 3-(1,2,3,6-tetrahydro-4-pyridinyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute the product. The product-containing fractions were concentrated in vacuum and the residue recrystallized from ethanol/ethyl acetate to give 4.45 g of the (S)-enantiomer of the title compound as a yellow solid (m.p. 210° C.).

Elemental Analysis for: C$_{26}$H$_{25}$N$_3$O$_2$; Calc'd: C, 75.89; H, 6.12; N, 10.21; Found: C, 75.51; H, 6.15; N, 10.14.

EXAMPLE 10

2-[4-(6-Fluoro-1H-indol-3-yl)-3,6-dihydro-2H-pyridin-1-ylmethyl]-8-methyl-2,3-dihydro[1,4]dioxino[2,3-f]quinoline To a solution of (2R)-8-methyl-2,3-dihydro[1,4]dioxino[2,3-f]quinolin-2-ylmethyl 4-methylbenzenesulfonate (0.50 g, 1.29 mmole) and potassium carbonate (0.35 g, 2.5 mmole) in 20 mL of 1:1 THF/DMF was added 0.55 g (2.5 mmole) of 6-fluoro-3-(1,2,3,6-tetrahydro-4-pyridinyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute the product. The product-containing fractions were concentrated in vacuum to give 0.31 g of yellow solid and the solid recrystallized from isopropanol with the addition of 0.09 g (0.99 mmole) of oxalic acid to give 0.050 g of the (S)-enantiomer of the title compound as a yellow solid dioxalate, dihydrate (m.p. 140–143° C.).

Elemental Analysis for: C$_{26}$H$_{24}$FN$_3$O$_2$.2 C$_2$H$_2$O$_4$.2 H$_2$O; Calc'd: C, 55.81; H, 5.00; N, 6.51; Found: C, 55.99; H, 4.66; N, 6.44.

EXAMPLE 11

2-[4-(5-Fluoro-1H-indol-3-yl)-3,6-dihydro-2H-pyridin-1-ylmethyl]-8-methyl-2,3-dihydro[1,4]dioxino[2,3-f]quinoline (2R)-8-Methyl-2,3-dihydro[1,4]dioxino[2,3-f]quinolin-2-ylmethyl-4-methylbenzenesulfonate (0.55 g, 1.42 mmole) and 5-fluoro-3-(1,2,3,6-tetrahydro-4-pyridinyl)-1H-indole (1.20 g, 5.56 mmole) were combined in 70 mL of DMSO. The mixture was heated at 75–80° C. under nitrogen for 6 hours. After cooling to room temperature, the mixture was partitioned between 400 mL each of ethyl acetate and saturated aqueous sodium bicarbonate. The organic phase was removed, washed with saturated brine, dried over magnesium sulfate, filtered and concentrated to dryness under vacuum. The residue was column chromatographed on silica gel using first methylene chloride to elute impurities and then 3% methanol in methylene chloride to elute the product. The product-containing fractions were concentrated in vacuum to give 0.52 g of yellow oil, which was recrystallized from ethanol with the addition of 0.33 g (2.8 mmole) of fumaric acid to give 0.23 g of the (S)-enantiomer of the title compound as a yellow solid monofumarate, dihydrate (m.p. 198–199° C.).

Elemental Analysis for: C$_{26}$H$_{24}$FN$_3$O$_2$.C$_4$H$_4$O$_4$.2 H$_2$O; Calc'd: C, 61.96; H, 5.55; N, 7.22; Found: C, 61.98; H, 5.58; N, 7.08.

EXAMPLE 12

2-[4-(1H-indol-3-yl)piperidin-1-ylmethyl]-8-methyl-2,3-dihydro[1,4]dioxino[2,3-f]quinoline To a solution of (2R)-8-methyl-2,3-dihydro[1,4]dioxino[2,3-f]quinolin-2-ylmethyl 4-methylbenzenesulfonate (0.57 g, 1.48 mmole) and potassium carbonate (0.70 g, 5.0 mmole) in 40 mL of 1:1 THF/DMF was added 1.00 g (5.00 mmole) of 3-(4-piperidinyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute the product. The product-containing fractions were concentrated in vacuum to give 0.40 g of yellow foam, which was crystallized from ethanol with the addition of 0.16 g (1.37 mmole) of fumaric acid to give 0.37 g of the (S)-enantiomer of the title compound as a yellow solid fumarate, hemihydrate (m.p. 206° C.).

Elemental Analysis for: C$_{26}$H$_{27}$N$_3$O$_2$.C$_4$H$_4$O$_4$.0.5 H$_2$O; Calc'd: C, 66.90; H, 5.99; N, 7.80; Found: C, 66.90; H, 5.97; N, 7.78.

INTERMEDIATE 12

{7-Nitro-8-[(E)-3-oxo-1-pentenyl]-2,3-dihydro-1,4-benzodioxin-2-yl}methyl 4-Methylbenzenesulfonate To a solution of 5.00 g (12.2 mmole) of [(2R)-8-formyl-7-nitro-2,3-dihydro-1,4-benzodioxin-2-yl]methyl 4-methylbenzenesulfonate in 200 mL of toluene was added 5.10 g (15.3 mmole) of 1-triphenylphosphoranylidene-2-butanone. The mixture was stirred at room temperature under nitrogen for 5 hours, after which time the solvent was removed in vacuum and the crude residue was column chromatographed on silica gel with methylene chloride as eluant to give 5.0 g of the (R)-enantiomer of the title compound as a yellow solid (m.p. 114° C.).

Elemental Analysis for: $C_{17}H_1SNO_8S$; Calc'd: C, 56.37; H, 4.73; N, 3.13; Found: C, 56.81; H, 4.60; N, 3.01.

INTERMEDIATE 13

(8-Ethyl-2,3-dihydro[1,4]dioxino[2,3-f]quinolin-2-yl)methyl 4-Methylbenzenesulfonate To a solution of {(2R)-7-nitro-8-[(E)-3-oxo-1-pentenyl]-2,3-dihydro-1,4-benzo-dioxin-2-yl}methyl 4-methylbenzenesulfonate (1.57 g, 3.50 mmole) in 100 mL of acetic acid/ethanol (1:1) was added 1.00 g (17.9 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 0.94 g of the (R)-enantiomer of the title compound as a yellow oil. $^1$H-NMR (CDCl$_3$): doublet 8.2 δ (1 H); doublet 7.8 δ (2 H); doublet 7.55 δ (1 H); 7.2–7.3 δ (4 H); multiplet 4.6 δ (1 H); multiplet 4.2–4.4 δ (3 H); multiplet 4.1 δ (1 H); quartet 3.0 δ (2 H); singlet 2.4 δ (3 H); triplet 1.4 δ (3 H).

EXAMPLE 13

8-Ethyl-2-[(4-(1H-indol-3-yl)-3,6-dihydropyridin-1(2H)-yl)methyl]-2,3-dihydro[1,4]dioxino[2,3-f]quinoline To a solution of (2R)-8-ethyl-2,3-dihydro[1,4]dioxino[2,3-f]quinolin-2-ylmethyl 4-methylbenzenesulfonate (0.60 g, 1.5 mmole) and potassium carbonate (0.65 g, 4.70 mmole) in 30 mL of 1:1 THF/DMF was added 0.90 g (4.5 mmole) of 3-(1,2,3,6-tetrahydro-4-pyridinyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute the product. The product-containing fractions were concentrated in vacuum and the residue recrystallized from ethanol to give 0.42 g of the (S)-enantiomer of the title compound as a yellow solid (m.p. 190° C.).

Elemental Analysis for: $C_{27}H_{27}N_3O_2$; Calc'd: C, 76.21; H, 6.40; N, 9.87; Found: C, 76.00; H, 6.43; N, 9.76.

EXAMPLE 14

8-Ethyl-2-[(4-(5-fluoro-1H-indol-3-yl)-3,6-dihydropyridin-1(2H)-yl)methyl]-2,3-dihydro[1,4]dioxino[2,3-f]quinoline To a solution of (2R)-8-ethyl-2,3-dihydro[1,4]dioxino[2,3-f]quinolin-2-ylmethyl 4-methylbenzenesulfonate (0.43 g, 1.07 mmole) and potassium carbonate (0.45 g, 3.20 mmole) in 30 mL of 1:1 THF/DMF was added 0.70 g (3.24 mmole) of 5-fluoro-3-(1,2,3,6-tetrahydro-4-pyridinyl)-1H-indole. The mixture was heated at reflux under nitrogen for 6 hours. After cooling to room temperature, the mixture was concentrated to dryness under vacuum and the residue column chromatographed on silica gel using first methylene chloride to elute impurities and then 3% methanol in methylene chloride to elute the product. The product-containing fractions were concentrated in vacuum to give 0.31 g of yellow solid, which was recrystallized from ethanol with the addition of 0.12 g (1.03 mmole) of fumaric acid to give 0.14 g of the (S)-enantiomer of the title compound as a yellow solid monofumarate, hydrate (m.p. 143–144° C.).

Elemental Analysis for: $C_{27}H_{26}FN_3O_2 \cdot C_4H_4O_4 \cdot H_2O$; Calc'd: C, 64.46; H, 5.58; N, 7.27; Found: C, 64.21; H, 5.50; N, 7.14.

INTERMEDIATE 14

[7-Nitro-6-fluoro-2,3-dihydro-1,4-benzodioxin-2y] methyl 4-Methylbenzenesulfonate To a solution of 19.0 g (56.2 mmole) of {(2R)-6-fluoro-2,3-dihydro-1,4-benzodioxin-2-yl}methyl 4-methylbenzenesulfonate in 200 mL of 1,2-dichloro-ethane in an ice/water bath was added dropwise a solution of 8.35 mL (0.197 mole) of fuming nitric acid (d 1.49) and the mixture was stirred for 2 hours at 0° C. After the reaction was complete, it was quenched with ice and diluted with 500 mL of methylene chloride. After the ice had melted, the organic layer was separated and washed with equal volumes of saturated aqueous sodium bicarbonate and saturated brine, dried over magnesium sulfate, filtered and concentrated in vacuum to a crude yellow solid. This was column chromatographed on silica gel with 1:1 hexane/methylene chloride as eluant to give 18.6 g of the (R)-enantiomer of the title compound as a light yellow solid (m.p. 106–107° C.).

Elemental Analysis for: $C_{16}H_{14}FNO_7S$; Calc'd: C, 50.13; H, 3.68; N, 3.65; Found: C, 50.13; H, 3.52; N, 3.54.

INTERMEDIATE 15

[7-Amino-6-fluoro-2,3-dihydro-1,4-benzodioxin-2y] methyl 4-Methylbenzenesulfonate To a mixture of 3.52 g (9.17 mmole) of [(2S)-7-nitro-6-fluoro-2,3-dihydro-1,4-benzodioxin-2y]methyl 4-methylbenzenesulfonate and 2.5 mL of 4 N isopropanolic HCl in 200 mL of ethyl acetate was added 0.50 g of 10% palladium on carbon and the mixture treated with 50 psi of hydrogen on a Parr apparatus for 15 hours. The catalyst was then removed by filtration through celite and the filtrate concentrated in vacuum to give 3.04 g of the (R)-enantiomer of the title compound as beige solid hydrochloride salt. $^1$H-NMR (DSMO-d$_6$): doublet 7.8 δ (2 H); doublet 7.5 δ (2 H); doublet 6.8 δ (1 H); doublet 6.55 δ (1 H); multiplet 4.4 δ (1 H); doublet of doublets 4.3 δ (1 H); multiplet 4.2 δ (2 H); multiplet 3.85 δ (1 H); singlet 2.4 δ (3 H).

INTERMEDIATE 16

6-Fluoro-2,3-dihydro[1,4]dioxino[2,3-f]quinolin-2-ylmethyl 4-Methylbenzenesulfonate To 1.06 g (2.72 mmole) of [(2S)-7-amino-6-fluoro-2,3-dihydro-1,4-benzodioxin-2y]methyl 4-methylbenzenesulfonate hydrochloride was added 100 mL of concentrated hydrochloric acid. Then 0.66 g (2.68 mmole) of p-chloranil was added with sufficient ethanol to wash down the solid. The heterogeneous mixture was heated to reflux and a solution of 0.25 g (4.45 mmole) of acrolein in 10 mL of ethanol was added dropwise. Reflux was continued for an additional 1 hour. The mixture was then allowed to come to room temperature and added to ice water. The solution was made basic with 1 N NaOH and extracted with methylene chloride. The extract was dried over magnesium sulfate, filtered and concentrated to a crude brown oil in vacuum. This was column chromatographed on silica gel with 1:1 hexane/ethyl acetate and the product-containing fractions concentrated in vacuum to give 0.60 g of the (R)-enantiomer of the title compound as a yellow oil. $^1$H-NMR (CDCl$_3$): doublet 8.6 δ (1 H); doublet 8.2 δ (1 H); doublet 7.75 δ (2 H); multiplet 7.4 δ (1 H); doublet 7.25 δ (2 H); doublet 7.0 δ (1 H); multiplet 4.58 δ (1 H); multiplet 4.2–4.4 δ (3 H); multiplet 4.2 δ (1 H); singlet 2.4 δ (1 H).

EXAMPLE 15

6-Fluoro-2-[(4-(5-fluoro-1H-indol-3-yl)-3,6-dihydropyridin-1(2H)-yl)methyl]-2,3-dihydro[1,4]dioxino[2,3-f]quinoline 0.50 g (1.54 mmole) of (2R)-6-fluoro-2,3-dihydro[1,4]dioxino[2,3-f]-quinolin-2-ylmethyl 4-methylbenzenesulfonate and 1.21 g (5.60 mmole) of 5-fluoro-3-(1,2,3,6-tetrahydro-4-pyridinyl)-1H-indole were combined in 100 mL of DMSO. The mixture was heated at 75–80° C. under nitrogen for 6 hours. After cooling to room temperature, the mixture was partitioned between 400 mL each of ethyl acetate and saturated aqueous sodium bicarbonate. The organic phase was removed, washed with saturated brine, dried over magnesium sulfate, filtered and concentrated to a crude oil under vacuum. This oil was column chromatographed on silica gel using first methylene chloride to elute impurities and then 2% methanol in methylene chloride to elute the product. The product-containing fractions were concentrated in vacuum to give 0.54 g of a yellow solid, which was recrystallized from ethanol with the addition of 0.17 g (1.5 mmole) of fumaric acid to give 0.265 g of the (S)-enantiomer of the title compound as a yellow solid hemifumarate one-quarter hydrate (m.p. 190° C.).

Elemental Analysis for: $C_{25}H_{21}F_2N_3O_2 \cdot 0.5 \ C_4H_4O_4 \cdot 0.25 \ H_2O$; Calc'd: C, 65.38; H, 4.78; N, 8.47; Found: C, 65.06; H, 4.50; N, 8.20.

EXAMPLE 16

6-Fluoro-2-[4-(1H-indol-3-yl)-3,6-dihydro-2H-pyridin-1-ylmethyl]-2,3-dihydro[1,4]dioxino[2,3-f]quinoline 0.40 g (1.02 mmole) of (2R)-6-fluoro-2,3-dihydro[1,4]dioxino[2,3-f]-quinolin-2-ylmethyl 4-methylbenzenesulfonate and 0.80 g (4.06 mmole) of 3-(1,2,3,6-tetrahydro-4-pyridinyl)-1H-indole were combined in 50 mL of DMSO. The mixture was heated at 75–80° C. under nitrogen for 6 hours. After cooling to room temperature, the mixture was partitioned between 400 mL each of ethyl acetate and saturated aqueous sodium bicarbonate. The organic phase was removed, washed with saturated brine, dried over magnesium sulfate, filtered and concentrated to a crude oil under vacuum. This oil was column chromatographed on silica gel using first 1% methanol in methylene chloride to elute impurities and then 5% methanol in methylene chloride to elute the product. The product-containing fractions were concentrated in vacuum to give 0.085 g of the (S)-enantiomer of the title compound as a yellow solid (m.p. 215° C.).

Elemental Analysis for: $C_{25}H_{22}FN_3O_2$; Calc'd: C, 72.27; H, 5.34; N, 10.11; Found: C, 71.88; H, 5.41; N, 10.19.

INTERMEDIATE 17

[7-Nitro-6-methoxy-2,3-dihydro-1,4-benzodioxin-2y]methyl 4-Methylbenzenesulfonate To a solution of 5.91 g (16.9 mmole) of {(2R)-6-methoxy-2,3-dihydro-1,4-benzodioxin-2-ylmethyl 4-methylbenzenesulfonate in 200 mL of 1,2-dichloro-ethane in an ice/water bath was added dropwise a solution of 2.50 mL (59.1 mmole) of fuming nitric acid (d 1.49) in 75 mL of 1,2-dichloroethane and the mixture was stirred for 2 hours at 0° C. After the reaction was complete, it was quenched with ice and diluted with 500 mL of methylene chloride. After the ice had melted, the organic layer was separated and washed with equal volumes of saturated aqueous sodium bicarbonate and saturated brine, dried over magnesium sulfate, filtered and concentrated in vacuum to give 6.19 g of the (R)-enantiomer of the title compound as a light yellow solid. $^1$H-NMR (CDCl$_3$): doublet 7.8 δ (2 H); multiplet 7.4 δ (3 H); singlet 6.5 δ (1 H); multiplet 4.10–4.5 δ (5 H); singlet 3.85 δ (3 H); singlet 2.5 δ (3 H).

INTERMEDIATE 18

[7-Amino-6-methoxy-2,3-dihydro-1,4-benzodioxin-2y]methyl 4-Methylbenzenesulfonate To a mixture of 3.74 g (9.40 mmole) of [(2S)-7-nitro-6-methoxy-2,3-dihydro-1,4-benzodioxin-2y]methyl 4-methylbenzenesulfonate and 2.5 mL of 4 N isopropanolic HCl in 200 mL of ethyl acetate was added 0.45 g of 10% palladium on carbon and the mixture treated with 50 psi of hydrogen on a Parr apparatus for 15 hours. The catalyst was then removed by filtration through celite and the filtrate concentrated in vacuum to give 3.41 g of the (R)-enantiomer of the title compound as beige solid hydrochloride salt. $^1$H-NMR (DSMO-d$_6$): broad singlet 9.8 δ (2 H); doublet 7.8 δ (2 H); doublet 7.45 δ (2 H); singlet 6.85 δ (1 H); singlet 6.75 δ (1 H); multiplet 4.2–4.45 δ (4 H); multiplet 4.0 δ (1 H); singlet 3.8 δ (3 H); singlet 2.5 δ (3 H).

INTERMEDIATE 19

6-Methoxy-2,3-dihydro[1,4]dioxino[2,3-f]quinolin-2-ylmethyl 4-Methylbenzenesulfonate To 1.50 g (3.73 mmole) of [(2S)-7-amino-6-methoxy-2,3-dihydro-1,4-benzodioxin-2y]methyl 4-methylbenzenesulfonate hydrochloride was added 100 mL of concentrated hydrochloric acid. Then 0.85 g (3.74 mmole) of 2,3-dichloro-1,4-naphthoquinone was added with sufficient ethanol to wash down the solid. The heterogeneous mixture was heated to reflux and a solution of 0.31 g (5.53 mmole) of acrolein in 10 mL of ethanol was added dropwise. Reflux was continued for an additional 1 hour. The mixture was then allowed to come to room temperature and added to ice water. The solution was made basic with 1 N NaOH and extracted with methylene chloride. The extract was dried over magnesium sulfate, filtered and concentrated to a crude brown oil in vacuum. This was column chromatographed on silica gel with a gradient elution commencing with methylene chloride and ending with 3% methanol in methylene chloride and the product-containing fractions concentrated in vacuum to give 0.75 g of the (R)-enantiomer of the title compound as a yellow oil. $^1$H-NMR (CDCl$_3$): doublet 8.8 δ (1 H); doublet 8.2 δ (1 H); doublet 7.8 δ (2 H); multiplet 7.4

δ (1 H); multiplet 7.2–7.25 δ (3 H); multiplet 4.45 δ (1 H); multiplet 4.1–4.4 δ (4 H); singlet 3.0 δ (3 H); singlet 2.4 δ (1 H).

EXAMPLE 17

2-[4-(5-Fluoro-1H-indol-3-yl)-3,6-dihydro-2H-pyridin-1-ylmethyl]-6-methoxy-2,3-dihydro[1,4]dioxino[2,3-f]qiuinoline 0.75 g (1.87 mmole) of (2R)-6-methoxy-2,3-dihydro[1,4]dioxino[2,3-f]-quinolin-2-ylmethyl 4-methylbenzenesulfonate and 1.41 g (6.55 mmole) of 5-fluoro-3-(1,2,3,6-tetrahydro-4-pyridinyl)-1H-indole were combined in 100 mL of DMSO. The mixture was heated at 75–80° C. under nitrogen for 6 hours. After cooling to room temperature, the mixture was partitioned between 400 mL each of ethyl acetate and saturated aqueous sodium bicarbonate. The organic phase was removed, washed with saturated brine, dried over magnesium sulfate, filtered and concentrated to a crude oil under vacuum. This oil was column chromatographed on silica gel using first methylene chloride to elute impurities and then 3% methanol in methylene chloride to elute the product. The product-containing fractions were concentrated in vacuum to give 0.47 g of a brown oil, which was crystallized from ethanol with the addition of 0.12 g (1.03 mmole) of fumaric acid to give 0.220 g of the (S)-enantiomer of the title compound as a yellow solid monofumarate, (m.p. 217° C.) containing 0.2 equivalents of ethanol.

Elemental Analysis for: $C_{26}H_{24}FN_3O_3 \cdot C_4H_4O_4 \cdot 0.2$ $C_2H_6O$; Calc'd: C, 62.02; H, 5.02; N, 7.48; Found: C, 65.21; H, 5.36; N, 7.75.

INTERMEDIATE 20

Toluene-4-sulfonic Acid 8-(3-Nitrilo-propenyl)-7-nitro-2,3-dihydro-benzo[1,4]dioxin-2-ylmethyl Ester To a suspension of 0.44 g (11 mmole) of 60% sodium hydride/mineral oil dispersion in 100 mL of DMF was add 1.8 g (10 mmole) of diethyl cyanomethylphosphonate. The mixture was stirred for 30 minutes at room temperature under nitrogen and then 3.0 g (7.6 mmole) of [(2R)-8-formyl-7-nitro-2,3-dihydro-1,4-benzodioxin-2-yl]methyl 4-methylbenzenesulfonate added and stirring at room temperature continued overnight. The solvent was then removed in vacuum and replaced with 400 mL of dichloromethane. The solution was washed with 300 mL portions of water and saturated brine, dried over sodium sulfate, filtered and concentrated in vacuum to a yellow oil. This was column chromatographed on silica gel with methylene chloride as eluant to give 2.5 g of the (R)-enantiomer of the title compound as a yellow solid (m.p. 117–118° C.).

Elemental Analysis for: $C_{19}H_{16}N_2O_7S$; Calc'd: C, 54.80; H, 3.87; N, 6.73; Found: C, 54.79; H, 3.90; N, 6.60.

INTERMEDIATE 21

(8-Amino-2,3-dihydro[1,4]dioxino[2,3-f]quinolin-2-yl)methyl 4-Methylbenzenesulfonate To a solution of 2.5 g (6.0 mmole) of toluene-4-sulfonic acid (2R)-8-(3-nitrilo-propenyl)-7-nitro-2,3-dihydro-benzo[1,4]dioxin-2-ylmethyl ester in 200 mL of ethyl acetate was added 6.8 g (30 mmole) of tin (II) chloride dihydrate and the mixture was refluxed under nitrogen for 5 hours. The solvent was then removed in vacuum and replaced with 250 mL of methanol. Concentrated HCl (5 mL) was added and the mixture was refluxed under a nitrogen atmosphere for 15 hours. The solvent was again removed in vacuum and 500 mL of saturated aqueous sodium bicarbonate added. This was extracted twice with 250 mL portions of ethyl acetate and the combined organics washed with 400 mL portions of water and saturated brine, dried over sodium sulfate, filtered and concentrated in vacuum. The residue was column chromatographed on silica gel with 5% methanol in chloroform as eluant to give 0.80 g of the (R)-enantiomer of the title compound as a yellow solid. $^1$H-NMR (CDCl$_3$): doublet 8.0 δ (1 H); doublet 7.8 δ (2 H); doublet 7.3 δ (2 H); doublet 7.2 δ (1 H); doublet 7.1 δ (1 H); doublet 6.7 δ (1 H); multiplet 4.5 δ (1 H); multiplet 4.3 δ (3 H); doublet of doublets 4.1 δ (1 H); singlet 2.4 δ (3 H).

EXAMPLE 18

2-[4-(5-Fluoro-1H-indol-3-yl)-3,6-dihydro-2H-pyridin-1-ylmethyl]-2,3-dihydro[1,4]dioxino[2,3-f]guinolin-8-ylamine (2R)-8-Amino-2,3-dihydro[1,4]dioxino[2,3-f]quinolin-2-ylmethyl 4-methylbenzenesulfonate (0.72 g, 1.9 mmole) and 5-fluoro-3-(1,2,3,6-tetrahydro-4-pyridinyl)-1H-indole (1.2 g, 5.5 mmole) were combined in 15 mL of DMSO and heated under nitrogen at 80° C. for 10 hours After cooling to room temperature, the mixture was diluted to 400 mL with ethyl acetate and washed with 300 mL of saturated aqueous sodium bicarbonate, twice with 300 mL portions of water and with 300 mL of saturated brine. The solution was dried over sodium sulfate, filtered and concentrated to dryness under vacuum. The residue was column chromatographed on silica gel using first chloroform and then 5% methanol as eluant. 0.30 g of the starting tosylate were eluted first. The later, product-containing fractions were concentrated in vacuum to give 0.13 g of yellow solid, which was recrystallized from ethanol with the addition of one equivalent of fumaric acid to give 0.090 9 of the (S)-enantiomer of the title compound as a gold solid monofumarate, dihydrate (m.p. 245° C.).

Elemental Analysis for: $C_{25}H_{23}FN_4O_2 \cdot C_4H_4O_4 \cdot 2\ H_2O$; Calc'd: C, 59.79; H, 5.36; N, 9.62; Found: C, 59.59; H, 5.13; N, 9.34.

EXAMPLE 19

2-({4-[(7-Ethyl-1H-indol-3-yl)methyl]piperidin-1-yl}methyl)-8-methyl-2,3-dihydro[1,4]dioxino[2,3-f]quinoline (2R)-8-Methyl-2,3-dihydro[1,4]dioxino[2,3-f]quinolin-2-ylmethyl 4-methylbenzenesulfonate (0.60 g, 1.6 mmole) and 7-ethyl-3-(1,2,3,6-tetrahydro-4-pyridinyl)-1H-indole (1.0 g, 4.4 mmole) were combined in 10 mL of DMSO. The mixture was heated at 70–80° C. under nitrogen for 6 hours. After cooling to room temperature, the mixture was partitioned between 400 mL each of ethyl acetate and saturated aqueous sodium bicarbonate. The organic phase was removed, washed with 400 mL portions of water and saturated brine, dried over sodium sulfate, filtered and concentrated to dryness under vacuum. The residue was column chromatographed on silica gel using 0–2% methanol/chloroform. The product fractions were concentrated in vacuum and the residue triturated with ether to give 0.16 g of the (S)-enantiomer of the title compound as a yellow solid, m.p. 85–90° C.

Elemental Analysis for: $C_{28}H_{29}N_3O_2 \cdot 0.40\ C_4H_{10}O \cdot 0.25\ H_2O$; Calc'd: C, 75.05; H, 7.13; N, 8.87; Found: C, 75.09; H, 7.1 1; N, 8.56.

EXAMPLE 20

2-({4-[(6-Chloro-1H-indol-3-yl)methyl]piperidin-1-yl}methyl)-8-methyl-2,3-dihydro[1,4]dioxino[2,3-f]quinoline

(2R)-8-Methyl-2,3-dihydro[1,4]dioxino[2,3-f]quinolin-2-ylmethyl 4-methylbenzenesulfonate (0.55 g, 1.4 mmole) and 6-chloro-3-(1,2,3,6-tetrahydro-4-pyridinyl)- 1H-indole (0.80 g, 3.4 mmole) were combined in 10 mL of DMSO. The mixture was heated at 70–80 ° C. under nitrogen for 6 hours. After cooling to room temperature, the mixture was partitioned between 400 mL each of ethyl acetate and saturated aqueous sodium bicarbonate. The organic phase was removed, washed with 400 mL portions of water and saturated brine, dried over sodium sulfate, filtered and concentrated to dryness under vacuum. The residue was column chromatographed on silica gel using 0–2% methanol/chloroform. The product fractions were concentrated in vacuum to give 0.27 g of the (S)-enantiomer of the title compound as an amorphous orange solid, which retains 0.35 equivalents of chloroform.

Elemental Analysis for: $C_{26}H_{24}ClN_3O_2 \cdot 0.35\ CHCl_3$; Calc'd: C, 64.89; H, 5.03; N, 8.62; Found: C, 65.00; H, 5.22; N, 8.26.

EXAMPLE 21

2-[4-(7-Fluoro-1H-indol-3-yl)-3,6-dihydro-2H-pyridin-1-ylmethyl-8-methyl-2,3-dihydro[1,4]dioxino[2,3-f]quinoline

(2R)-8-Methyl-2,3-dihydro[1,4]dioxino[2,3-f]quinolin-2-ylmethyl 4-methylbenzene sulfonate (0.55 g, 1.4 mmole) and 7-fluoro-3-(1,2,3,6-tetrahydro-4-pyridinyl)-1H-indole (0.80 g, 3.7 mmole) were combined in 10 mL of DMSO. The mixture was heated at 70–80° C. under nitrogen for 6 hours. After cooling to room temperature, the mixture was partitioned between 400 mL each of ethyl acetate and saturated aqueous sodium bicarbonate. The organic phase was removed, washed with 400 mL portions of water and saturated brine, dried over sodium sulfate, filtered and concentrated to dryness under vacuum. The residue was column chromatographed on silica gel using 0–2% methanol/chloroform. The product fractions were concentrated in vacuum to give 0.39 g of the (S)-enantiomer of the title compound as a pale yellow solid (m.p. 205–21 0° C.), which retains 0.25 equivalents of chloroform.

Elemental Analysis for: $C_{26}H_{24}FN_3O_2 \cdot 0.25\ CHCl_3$; Calc'd: C, 68.64; H, 5.32; N, 9.15; Found: C, 68.83; H, 5.37; N, 8.90.

EXAMPLE 22

2-[4-(5-Methyl-1H-indol-3-yl)-3,6-dihydro-2H-pyridin-1-ylmethyl]-8-methyl-2,3-dihydro[1,4]dioxino[2,3-f]quinoline

(2R)-8-Methyl-2,3-dihydro[1,4]dioxino[2,3-f]quinolin-2-ylmethyl 4-methylbenzenesulfonate (0.55 g, 1.4 mmole) and 5-methyl-3-(1,2,3,6-tetrahydro-4-pyridinyl)-1H-indole (0.80 g, 3.8 mmole) were combined in 10 mL of DMSO. The mixture was heated at 70–80 ° C. under nitrogen for 6 hours. After cooling to room temperature, the mixture was partitioned between 400 mL each of ethyl acetate and saturated aqueous sodium bicarbonate. The organic phase was removed, washed with saturated brine, dried over magnesium sulfate, filtered and concentrated to dryness under vacuum. The residue was column chromatographed on silica gel using 0–2% methanol/chloroform as eluant. The product-containing fractions were concentrated in vacuum and the residue recrystallized from isopropanol with the addition of fumaric acid to give 0.32 g of the (S)-enantiomer of the title compound as a yellow solid monofumarate, three-quarter hydrate (m.p. 150–155° C.).

Elemental Analysis for: $C_{27}H_{27}N_3O_2 \cdot C_4H_4O_4 \cdot 0.75\ H_2O$; Calc'd: C, 67.07; H, 5.90; N, 7.57; Found: C, 66.68; H, 5.91; N, 7.29.

INTERMEDIATE 22

(9-Methyl-2,3-dihydro[1,4]dioxino[2,3-f]quinolin-2-yl)methyl 4-Methylbenzenesulfonate

To a mixture of 1.00 g (2.5 mmole) of [(2R)-8-formyl-7-nitro-2,3-dihydro-1,4-benzodioxin -2-yl]methyl 4-methylbenzenesulfonate, 0.35 g (2.5 mmole) of potassium carbonate and 0.31 g (1.7 mmole) of benzyltrimethylammonium chloride in 5 mL of methylene chloride was added 0.145 g (2.5 mmole) of propionaldehyde. The mixture was stirred at room temperature under nitrogen for 15 hours, then diluted with 100 mL of water and extracted twice with 100 mL portions of methylene chloride. The combined organic extracts were washed with 100 mL of saturated brine, dried over sodium sulfate, filtered and concentrated in vacuum. The crude residue was column chromatographed on silica gel with methylene chloride as eluant to give 0.50 g of the (R)-enantiomer of toluene-4-sulfonic acid 8-(2-methyl-3-oxo-propenyl)-7-nitro-2,3-dihydro-benzo[1,4]dioxin-2-ylmethyl ester as a yellow oil. This was dissolved in a mixture of 12 mL of acetic acid and 8 mL of ethanol and 0.32 g (5.7 mmole) of iron powder was added. The mixture was refluxed for eight hours under nitrogen. The solvent was then removed in vacuum and replaced with 250 mL of ethyl acetate. This mixture was washed with 250 mL portions of saturated aqueous sodium bicarbonate and saturated brine, dried over sodium sulfate, filtered and concentrated in vacuum. Column chromatography on silica gel with chloroform as eluant gave 0.22 g of the (R)-enantiomer of the title compound as a yellow oil. $^1$H-NMR (CDCl$_3$): doublet (m-coupling) 8.6 δ (1 H); doublet (m-coupling) 8.0 δ (1 H); doublet 7.76 8 (2 H); doublet 7.57 δ (1 H); doublet 7.24 δ (1 H); doublet 7.20 δ (2 H); multiplet 4.55 δ (1 H); doublet of doublets 4.3 δ (1 H); multiplet 4.2 δ (2 H); doublet of doublets 4.15 δ (1 H); singlet 2.5 δ (3H); singlet 2.4 δ (3 H).

EXAMPLE 23

2-[4-(1H-Indol-3-yl)-3,6-dihydro-2H-pyridin-1-ylmethyl]-9-methyl-2,3-dihydro[1,4]dioxino[2,3-f]quinoline

(2R)-9-Methyl-2,3-dihydro[1,4]dioxino[2,3-f]quinolin-2-ylmethyl 4-methyl benzenesulfonate (0.22 g, 0.57 mmole) and 3-(1,2,3,6-tetrahydro-4-pyridinyl)-1H-indole (0.40 g, 2.0 mmole) were combined in 10 mL of DMSO and heated under nitrogen at 80° C. for 6 hours. The mixture was diluted with 300 mL of ethyl acetate, washed with 300 mL portions of saturated aqueous sodium bicarbonate and saturated brine, dried over sodium sulfate, filtered and concentrated to an oil in vacuum. The crude oil was column chromatographed on silica gel using first chloroform and then 1% methanol/chloroform as eluant. The product-containing fractions were concentrated in vacuum to 0.12 g of free base, which was triturated with methylene chloride/hexane to give 0.04 g of the (S)-enantiomer of the title compound as a pale yellow solid (m.p. 211–213° C.).

Elemental Analysis for: $C_{26}H_{25}N_3O_2 \cdot 0.25\ CH_2Cl_2 \cdot 0.50\ H_2O$; Calc'd: C, 71.37; H, 6.05; N, 9.51; Found: C, 71.12; H, 6.04; N, 9.24.

EXAMPLE 24

8-Ethyl-2-[4-(1H-indol-3-yl)-piperidin-1-ylmethyl]-2,3-dihydro-1,4]dioxino[2,3-f]quinoline To a mixture of 0.25 g (0.59 mmole) of (2S)-8-ethyl-2-[(4-(1H-indol-3-yl)-3,6-dihydropyridin-1(2H)-yl)methyl]-2,3-dihydro[1,4]dioxino[2,3-f]quinoline and 0.2 g of 10% palladium on carbon in 100 mL of methanol was added 0.2 mL of concentrated HCl. The mixture was treated with 60 psi of hydrogen in a Parr apparatus for 15 hours. It was then filtered through celite and concentrated to an oil in vacuum. Ethyl acetate (300 mL) was added and the mixture was washed with 300 mL portions of saturated aqueous sodium bicarbonate and saturated brine, dried over sodium sulfate, filtered and concentrated in vacuum. Column chromatography on silica gel with 0–2% methanol/chloroform as eluant gave 0.19 g of the title compound as the free base. Recrystallization from ethanol with the addition of 0.052 g of fumaric acid gave 0.15 g of the (S)-enantiomer of the title compound as an off-white fumarate (m.p. 169–172° C.).

What is claimed is:

1. A compound of formula I:

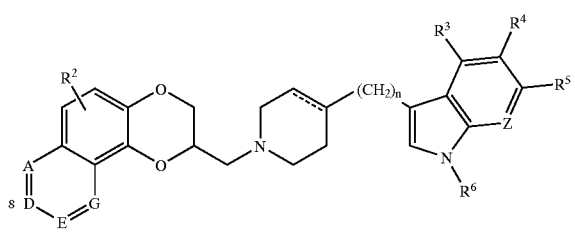

wherein $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms $R^6$ is hydrogen or alkyl of 1 to 6 carbon atoms;

A dotted line represents an optional double bond;

A and D are selected from carbon substituted by $R^1$ and nitrogen, provided that at least one of A and D is nitrogen;

E and G are carbon, substituted by $R^1$;

Z is N or $CR^7$; and n is an integer 0, 1 or 2; or pharmaceutically acceptable salts thereof.

2. A compound of Formula Ia

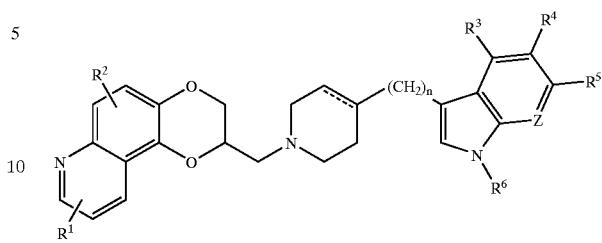

wherein:

$R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms $R^6$ is hydrogen or alkyl of 1 to 6 carbon atoms;

A dotted line represents an optional double bond;

Z is N or $CR^7$; and n is an integer 0, 1 or 2; or pharmaceutically acceptable salts thereof.

3. A compound of claim 2 wherein $R^1$ is hydrogen, hydroxy, halogen, alkyl of 1 to 6 carbon atoms, amino, mono- or di-alkylamino in which each alkyl group has 1 to 6 carbon atoms.

4. A compound of claim 2 wherein $R^1$ is substituted at the 8-position.

5. A compound of claim 2 wherein $R^2$ is hydrogen, hydroxy, halo, cyano, trifluoromethyl, alkyl of 1 to 6 carbon atoms or alkoxy of one to six carbon atoms.

6. A compound of claim 2 wherein $R^3$, $R^4$, $R^5$ and $R^7$ are, independently selected from hydrogen, hydroxy, halogen, cyano, carboxamido, alkyl of one to six carbon atoms, or alkoxy of one to six carbon atoms.

7. A compound of claim 2 wherein $R^2$ and $R^6$ are hydrogen, $R^3$, $R^4$, $R^5$ and $R^7$ are, independently selected from hydrogen, halogen or cyano, n is 0 and the dotted line represents a double bond.

8. The compound of claim 1 which is 2-[4-(5-methoxy-1H-indol-3-yl)-3,6-dihydro-2H-pyridin-1-ylmethyl]-2,3-dihydro[1,4]dioxino[2,3-f]quinoline or a pharmaceutically acceptable salt thereof.

9. The compound of claim 1 which is 2-[4-(5-fluoro-1H-indol-3-yl)-3,6-dihydro-2H-pyridin-1-ylmethyl]-2,3-dihydro[1,4]dioxino[2,3-f]quinoline or a pharmaceutically acceptable salt thereof.

10. The compound of claim 1 which is [4-(5-fluoro-1H-indol-3-ylmethyl)-piperidin-1-ylmethyl]-2,3-dihydro[1,4]dioxino[2,3-f]quinoline or a pharmaceutically acceptable salt thereof.

11. The compound of claim 1 which is 2-[4-(1H-indol-3-yl)-3,6-dihydro-2H-pyridin-1-ylmethyl]-2,3-dihydro[1,4]dioxino[2,3-f]quinoline or a pharmaceutically acceptable salt thereof.

12. The compound of claim 1 which is 3-[1-(2,3-dihydro[1,4]dioxino[2,3-f]quinolin-2-ylmethyl)-1,2,3,6-tetrahydropyridin-4-yl]-1H-indole-5-carbonitrile or a pharmaceutically acceptable salt thereof.

13. The compound of claim 1 which is 3-[1-(2,3-dihydro[1,4]dioxino[2,3-f]quinolin-2-ylmethyl)-1,2,3,6-tetrahydropyridin-4-yl]-1H-indole-5-carboxylic acid amide or a pharmaceutically acceptable salt thereof.

14. The compound of claim 1 which is 2-[4-(5-fluoro-1-methyl-1H-indol-3-yl)-3,6-dihydro-2H-pyridin-1-ylmethyl]-2,3-dihydro[1,4]dioxino[2,3-f]quinoline or a pharmaceutically acceptable salt thereof.

15. The compound of claim 1 which is 2-({4-[(5-fluoro-1H-indol-3-yl)methyl]piperidin-1-yl}methyl)-8-methyl-2,3-dihydro[1,4]dioxino[2,3-f]-quinoline or a pharmaceutically acceptable salt thereof.

16. The compound of claim 1 which is 2-[4-(1H-indol-3-yl)-3,6-dihydro-2H-pyridin-1-ylmethyl]-8-methyl-2,3-dihydro[1,4]dioxino[2,3-f]quinoline or a pharmaceutically acceptable salt thereof.

17. The compound of claim 1 which is 2-[4-(6-fluoro-1H-indol-3-yl)-3,6-dihydro-2H-pyridin-1-ylmethyl]-8-methyl-2,3-dihydro[1,4]dioxino[2,3-f]-quinoline or a pharmaceutically acceptable salt thereof.

18. The compound of claim 1 which is 2-[4-(5-fluoro-1H-indol-3-yl)-3,6-dihydro-2H-pyridin-1-ylmethyl]-8-methyl-2,3-dihydro[1,4]dioxino[2,3-f]quinoline or a pharmaceutically acceptable salt thereof.

19. The compound of claim 1 which is 2-[4-(1H-indol-3-yl)piperidin-1-ylmethyl]-8-methyl-2,3-dihydro[1,4]dioxino[2,3-f]quinoline or a pharmaceutically acceptable salt thereof.

20. The compound of claim 1 which is 8-ethyl-2-[(4-(1H-indol-3-yl)-3,6-dihydropyridin-1(2H)-yl)methyl]-2,3-dihydro[1,4]dioxino[2,3-f]quinoline or a pharmaceutically acceptable salt thereof.

21. The compound of claim 1 which is 8-ethyl-2-[(4-(5-fluoro-1H-indol-3-yl)-3,6-dihydropyridin-1(2H)-yl)methyl]-2,3-dihydro[1,4]dioxino[2,3-f]quinoline or a pharmaceutically acceptable salt thereof.

22. The compound of claim 1 which is 6-fluoro-2-[(4-(5-fluoro-1H-indol-3-yl)-3,6-dihydropyridin-1(2H)-yl)methyl]-2,3-dihydro[1,4]dioxino[2,3-f]quinoline or a pharmaceutically acceptable salt thereof.

23. The compound of claim 1 which is 6-fluoro-2-[4-(1H-indol-3-yl)-3,6-dihydro-2H-pyridin-1-ylmethyl]-2,3-dihydro[1,4]dioxino[2,3-f]quinoline or a pharmaceutically acceptable salt thereof.

24. The compound of claim 1 which is 2-[4-(5-fluoro-1H-indol-3-yl)-3,6-dihydro-2H-pyridin-1-ylmethyl]-6-methoxy-2,3-dihydro[1,4]dioxino[2,3-f]quinoline or a pharmaceutically acceptable salt thereof.

25. The compound of claim 1 which is 2-[4-(5-fluoro-1H-indol-3-yl)-3,6-dihydro-2H-pyridin-1-ylmethyl]-2,3-dihydro[1,4]dioxino[2,3-f]quinolin-8-ylamine or a pharmaceutically acceptable salt thereof.

26. The compound of claim 1 which is 2-({4-[(7-Ethyl-1H-indol-3-yl)methyl]-piperidin-1-yl}methyl)-8-methyl-2,3-dihydro[1,4]dioxino[2,3-f]quinoline or a pharmaceutically acceptable salt thereof.

27. The compound of claim 1 which is 2-({4-[(6-Chloro-1H-indol-3-yl)-methyl]piperidin-1-yl}methyl)-8-methyl-2,3-dihydro[1,4]dioxino[2,3-f]quinoline or a pharmaceutically acceptable salt thereof.

28. The compound of claim 1 which is 2-[4-(7-Fluoro-1H-indol-3-yl)-3,6-dihydro-2H-pyridin-1-ylmethyl]-8-methyl-2,3-dihydro[1,4]dioxino[2,3-f]-quinoline or a pharmaceutically acceptable salt thereof.

29. The compound of claim 1 which is 2-[4-(5-Methyl-1H-indol-3-yl)-3,6-dihydro-2H-pyridin-1-ylmethyl]-8-methyl-2,3-dihydro[1,4]dioxino[2,3-f]-quinoline; and pharmaceutically acceptable salts thereof.

30. The compound of claim 1 which is 2-[4-(1H-indol-3-yl)-3,6-dihydro-2H pyridin-1-ylmethyl]-9-methyl-2,3-dihydro[1,4]dioxino[2,3-f]quinoline, and pharmaceutically acceptable salts thereof.

31. The compound of claim 1 which is 8-Ethyl-2-[4-(1H-indol-3-yl)-piperidin-1-ylmethyl]-2,3-dihydro-[1,4]dioxino[2,3-f]quinoline, and pharmaceutically acceptable salts thereof.

32. A compound of claim 1 which is the S enantiomer, substantially free of the R enantiomer of said compound.

33. A compound of Formula II

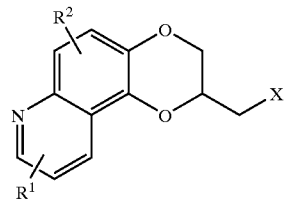

wherein

R¹ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R² is hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; and X is halogen, hydroxy, alkylsulfonate of 1 to 6 carbon atoms, trifluoromethanesulfonate or benzenesulfonate, in which the benzene ring is optionally substituted with halogen, hydroxy, nitro, trifluoromethyl, cyano, alkyl of 1 to 6 carbon atoms or alkoxy of 1 to 6 carbon atoms.

34. A compound of claim 33 which is:

2,3-Dihydro[1,4]dioxino[2,3-f]quinolin-2-ylmethyl 4-methylbenzenesulfonate;

(8-Methyl-2,3-dihydro[1,4]dioxino[2,3-f]quinolin-2-yl)methyl 4-methylbenzenesulfonate;

(8-Ethyl-2,3-dihydro[1,4]dioxino[2,3-f]quinolin-2-yl)methyl 4-methylbenzenesulfonate;

6-Fluoro-2,3-dihydro[1,4]dioxino[2,3-f]quinolin-2-ylmethyl 4-methylbenzenesulfonate;

6-Methoxy-2,3-dihydro[1,4]dioxino[2,3-f]quinolin-2-ylmethyl 4-methylbenzenesulfonate;

(8-Amino-2,3-dihydro[1,4]dioxino[2,3-f]quinolin-2-yl)methyl 4-methylbenzenesulfonate; or 9-Methyl-2,3-dihydro[1,4]dioxino[2,3-f]quinolin-2-yl)methyl 4-methylbenzenesulfonate.

35. A method of treating a subject suffering from a condition selected from depression, anxiety, panic disorder, obsessive compulsive disorder, social anxiety disorder and generalized anxiety disorder which comprises providing to the subject suffering from said condition, a therapeutically effective amount of a compound of formula I:

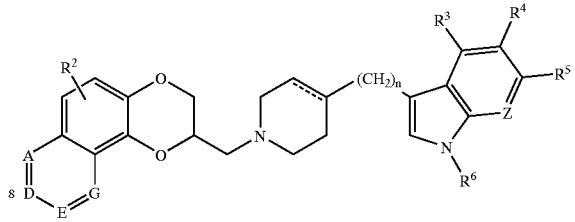

wherein

R¹ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R², R³, R⁴, R⁵ and R⁷ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms R⁶ is hydrogen or alkyl of 1 to 6 carbon atoms;

A dotted line represents an optional double bond;

A and D are selected from carbon substituted by R¹ and nitrogen, provided that at least one of A and D is nitrogen;

E and G are carbon, substituted by R¹;

Z is N or CR⁷; and n is an integer 0, 1 or 2; or pharmaceutically acceptable salts thereof.

36. The method of claim 35 wherein the condition is depression.

37. The method of claim 35 wherein the condition is selected from the group consisting of obsessive compulsive disorder, panic attacks, generalized anxiety disorder, and social anxiety disorder.

38. The method of claim 35 wherein the subject is a human.

39. A method of treating a subject suffering from a condition selected from depression, anxiety, panic disorder, obsessive compulsive disorder, social anxiety disorder and generalized anxiety disorder, which comprises providing to the subject suffering from said condition, a therapeutically effective amount of a compound of claim 2.

40. The method of claim 39 wherein the subject is a human.

41. A pharmaceutical composition comprising an effective amount of a compound of formula I:

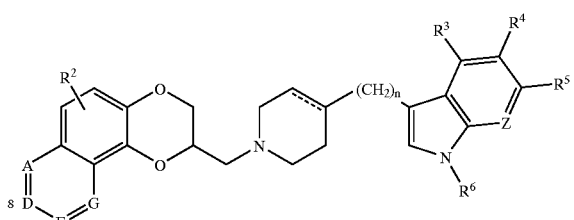

wherein

R¹ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R², R³, R⁴, R⁵ and R⁷ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms R⁶ is hydrogen or alkyl of 1 to 6 carbon atoms;

A dotted line represents an optional double bond;

A and D are selected from carbon substituted by R¹ and nitrogen, provided that at least one of A and D is nitrogen;

E and G are carbon, substituted by R¹;

Z is N or CR⁷; and n is an integer 0, 1 or 2; or pharmaceutically acceptable salts thereof.

42. A pharmaceutical composition comprising an effective amount of a compound of claim 2 and a pharmaceutically acceptable carrier or excipient.

* * * * *